(12) United States Patent
Nakka David et al.

(10) Patent No.: US 10,773,008 B2
(45) Date of Patent: Sep. 15, 2020

(54) MEDICATED PATCH FOR PREVENTING EXIT SITE INFECTIONS DURING PERITONEAL DIALYSIS

(71) Applicant: Universiti Brunei Darussalam, Gadong (BN)

(72) Inventors: Sheba Rani Nakka David, Gadong (BN); Rajan Rajabalaya, Gadong (BN)

(73) Assignee: UNIVERSITI BRUNEI DARUSSALAM, Gadong (BN)

(*) Notice: Subject to any disclaimer, the term of this patent is extended or adjusted under 35 U.S.C. 154(b) by 25 days.

(21) Appl. No.: 15/672,141

(22) Filed: Aug. 8, 2017

(65) Prior Publication Data

US 2018/0126058 A1 May 10, 2018

(30) Foreign Application Priority Data

Aug. 8, 2016 (BN) .................. BN/N/2016/0060

(51) Int. Cl.
*A61M 1/28* (2006.01)
*A61M 25/02* (2006.01)
*A61M 25/00* (2006.01)

(52) U.S. Cl.
CPC ............ *A61M 1/285* (2013.01); *A61M 25/02* (2013.01); *A61M 2025/0056* (2013.01); *A61M 2025/0266* (2013.01); *A61M 2202/20* (2013.01); *A61M 2205/0205* (2013.01)

(58) Field of Classification Search
CPC .. A61M 1/285; A61M 25/02; A61M 25/0017; A61M 2025/0266; A61M 2202/20; A61M 2202/0205; A61M 39/10; A61B 17/085
See application file for complete search history.

(56) References Cited

U.S. PATENT DOCUMENTS

| 2,714,382 | A | * | 8/1955 | Alcala | A61F 13/0203 604/306 |
| 2,976,576 | A | * | 3/1961 | Drahoslav | A61L 15/60 204/296 |
| 3,007,571 | A | * | 11/1961 | Marinaro | A61F 13/0203 206/441 |
| 3,072,249 | A | * | 1/1963 | Tritsch | A61F 13/0203 206/441 |
| 3,580,254 | A | * | 5/1971 | Stuart | A61F 13/0203 206/441 |
| 3,598,122 | A | * | 8/1971 | Zaffaroni | A61F 9/0017 424/435 |

(Continued)

*Primary Examiner* — Nathan R Price
*Assistant Examiner* — Mark A Igel
(74) *Attorney, Agent, or Firm* — Sinorica, LLC

(57) ABSTRACT

A medicated apparatus including a medicated patch for use onto a subject undergoing peritoneal dialysis is disclosed, according to an embodiment of a present invention. The patch includes a medication layer containing a medication therein, and a backing film disposed on one side of the medication layer. The patch also includes a skin adhesive layer disposed beneath the medication layer; and a protective liner disposed beneath the skin adhesive layer. The patch is placed on a catheter by applying pressure to skin of a subject after insertion of the catheter therein, thereby holding the catheter and the medication diffusing into the skin prevents an exit site of infection.

15 Claims, 2 Drawing Sheets

(56) References Cited

U.S. PATENT DOCUMENTS

| | | | | |
|---|---|---|---|---|
| 3,598,123 A * | 8/1971 | Zaffaroni | A61K 9/7061 | 401/132 |
| 4,588,400 A * | 5/1986 | Ring | A61L 15/28 | 424/447 |
| 4,689,044 A * | 8/1987 | Murata | A61F 13/0203 | 604/306 |
| 4,743,249 A * | 5/1988 | Loveland | A61K 9/7084 | 424/447 |
| 4,767,411 A * | 8/1988 | Edmunds | A61M 25/02 | 128/DIG. 26 |
| 4,909,244 A * | 3/1990 | Quarfoot | A61F 13/023 | 424/78.06 |
| 5,109,874 A * | 5/1992 | Bellingham | A61F 15/004 | 128/888 |
| 5,115,801 A * | 5/1992 | Cartmell | A61F 13/023 | 128/888 |
| 5,204,110 A * | 4/1993 | Cartmell | A61F 13/023 | 424/443 |
| 5,236,421 A * | 8/1993 | Becher | A61M 25/02 | 602/54 |
| 5,419,913 A * | 5/1995 | Podell | A61C 15/041 | 424/448 |
| 5,533,962 A * | 7/1996 | Peterman | A61F 13/0203 | 602/41 |
| 6,461,644 B1 * | 10/2002 | Jackson | A61K 9/1635 | 424/499 |
| 6,897,348 B2 * | 5/2005 | Malik | A61K 31/375 | 424/447 |
| 9,889,091 B1 * | 2/2018 | Daneshvar | A61K 9/02 | |
| 2005/0232957 A1 * | 10/2005 | Katz | A61Q 19/007 | 424/401 |
| 2007/0287968 A1 * | 12/2007 | Daneshvar | A61K 9/0031 | 604/285 |
| 2008/0226701 A1 * | 9/2008 | Deignan | A61F 15/00 | 424/449 |
| 2008/0274166 A1 * | 11/2008 | Sacks | A61K 9/703 | 424/449 |
| 2009/0221947 A1 * | 9/2009 | Uematsu | A61F 13/023 | 602/57 |
| 2009/0263346 A1 * | 10/2009 | Taft | A61K 9/146 | 424/78.17 |
| 2010/0092546 A1 * | 4/2010 | Gurtner | A61K 9/06 | 424/449 |
| 2010/0241089 A1 * | 9/2010 | Uchiyama | A61F 7/034 | 604/291 |
| 2011/0009571 A1 * | 1/2011 | Taft | A61P 25/18 | 525/450 |
| 2011/0052664 A1 * | 3/2011 | Tennican | A61F 13/00063 | 424/445 |
| 2011/0098620 A1 * | 4/2011 | Dever | A61F 13/064 | 602/44 |

* cited by examiner

MEDICATED PATCH FOR PREVENTING EXIT SITE INFECTIONS DURING PERITONEAL DIALYSIS

RELATED APPLICATION

This application claims the benefit of Brunei Application No. BN/N/2016/0060 filed on Aug. 8, 2016 and entitled "A Medicated Tape for Preventing Exit Site Infections During Peritoneal Dialysis, the content of which is incorporated in its entirety herein by reference.

FIELD OF INVENTION

The present invention relates generally to a medicated patch and more particularly, the present invention relates to a medicated surgical patch for preventing exit site infections during peritoneal dialysis. Such infections can otherwise lead to serious infection of peritonitis. Moreover, the present invention also relates to a medicated surgical patch for preventing infections which can occur laparascopic surgical incisions or other incisions.

BACKGROUND OF THE INVENTION

Patients with severe chronic kidney disease require dialysis e.g. Peritoneal Dialysis (PD). PD involves exchange of fluids and dissolved substances from the blood using the patient's peritoneum in the abdomen. The PD requires access to the peritoneal cavity where the peritoneal dialysis catheter is inserted which acts as a permanent pathway into the peritoneal cavity. The permanent catheter involves exchange of fluids and dissolved substances from the blood. The catheter is usually placed just below the side of the belly button. The catheter exit site is usually covered with a dressing and the catheter is taped to the skin to avoid infections and pulling on the exit site. However, frequent changing of the catheter involves repetitive adhering and removing tape from the skin, which may lead to serious skin inflammation. In addition, increased duration of PD may cause morphological changes in the peritoneal membrane. For example, inadequate solute clearance, ultrafiltration failure (UFF) and changes in peritoneal membrane transport properties may cause progressive damage to the peritoneal membrane, thereby leading to inability of the membrane to function properly. Such changes may also lead to Exit Site Infections (ESIs) and peritonitis.

In another instance, the catheter and the surgical dressing can also be contaminated by bacteria such as *S. aureus* or fungi, which can lead to an infection of the peritoneum thereby leading to ESIs and peritonitis.

Conventional arts such as topical mupirocin can reduce the risk of *S. aureus* induced ESIs and peritonitis. However, the topical mupirocin has a poor bioavailability 0.24% and has a short half-life of about 20-40 minutes, requiring repeated administration. Thus, such administration may lead to the development of antibiotic resistance in patients. In addition, the ointment contains alcohol which can degrade the catheter, leading to cracks in the catheter. Therefore, catheter needs to be changed frequently which can cause inconvenience to patients and skin inflammations.

Therefore, there exists a need for developing an alternative over the conventional arts which can prevent ESIs and peritonitis.

SUMMARY OF THE INVENTION

In an aspect, a medicated apparatus including a medicated patch for use onto a subject undergoing peritoneal dialysis is disclosed. According to an embodiment of a present invention. The patch includes a medication layer containing a medication therein, and a backing film disposed on one side of the medication layer. The patch also includes a skin adhesive layer disposed beneath the medication layer; and a protective liner disposed beneath the skin adhesive layer. The patch is placed on a catheter by applying pressure to skin of a subject after insertion of the catheter therein, thereby holding the catheter and the medication diffusing into the skin prevents the infection of exit site.

In another aspect of the present invention, a method for preventing transdermal infections during transdermal drug delivery procedures is disclosed. The method includes loading a medicated patch with a medication. The patch includes a medication layer containing a medication therein, and a backing film disposed on one side of the medication layer. The patch also includes a skin adhesive layer disposed beneath the medication layer; and a protective liner disposed beneath the skin adhesive layer. The patch is placed on a catheter by applying pressure to the medicated patch on skin of a subject after insertion of the catheter therein. The medication gets diffused into the skin for treating an exit site infection of peritonitis during peritoneal dialysis.

BRIEF DESCRIPTION OF DRAWINGS

Other objects, features, and advantages of the invention will be apparent from the following description when read with reference to the accompanying drawings. In the drawings, wherein like reference numerals denote corresponding parts throughout the several views.

DETAILED DESCRIPTION OF THE PREFERRED EMBODIMENTS

Reference will now be made in detail to the preferred embodiments of the present invention, examples of which are illustrated in the accompanying drawings.

In the following detailed description, numerous specific details are set forth in order to provide a thorough understanding of the invention. However, it will be understood by those or ordinary skill in the art that the invention may be practiced without these specific details. In other instances, well known methods, procedures and/or components have not been described in detail so as not to obscure the invention.

The embodiment will be more clearly understood from the following description of the methods thereof, given by way of example only with reference to the accompanying drawings.

Figure 1A:
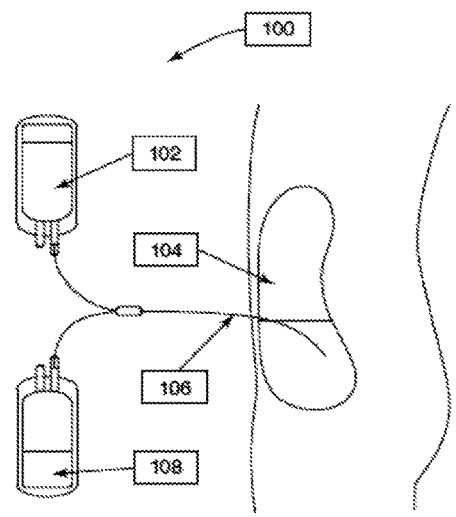
FIG. 1A depicts a schematic diagram of a peritoneal dialysis already known in the art.

PD for patients with severe chronic kidney diseases requiring peritoneal dialysis involves access to the peritoneal cavity wherein the catheter is inserted. As shown in FIG. 1A, PD 100 involves insertion of a catheter 106 into a peritoneal cavity 104. Dialysis fluid 102 is introduced through the catheter 106 in the peritoneal cavity 104 and waste fluid 108 is flushed out through the catheter 106.

Figure 1B:
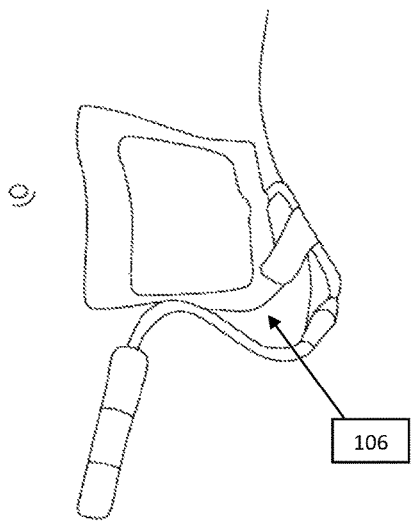
FIG. 1B depicts an image of a medicated patch from the art during peritoneal dialysis.
Figure 1C:
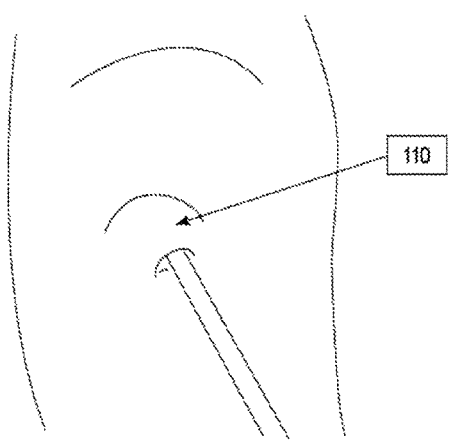
FIG. 1C depicts an image of an exit site infection using medicated patch of the art.

As shown further in FIG. 1B, the catheter 106 exit site is covered with a dressing and the catheter 106 is taped to the skin to avoid infections. However, frequent changing of catheter 106 can lead to ESIs and peritonitis as shown in FIG. 1C.

As already known in the art, topical mupirocin can reduce the risk of *S. aureus* induced ESIs and peritonitis. However, the topical mupirocin has a poor bioavailability of 0.24% and has a short half-life of about 20-40 minutes, requiring repeated administration. Thus, such administration may lead to the development of antibiotic resistance in patients. In addition, the ointment contains alcohol which can degrade the catheter leading to cracks in the catheter. Therefore, catheter needs to be changed frequently which can cause inconvenience to patients and skin inflammations.

However, if a self-adhesive medicated patch having mupirocin is applied on the exit site, then ESI can not only be used to prevent entry of bacteria but also can be applied nearest to the site of action. As already known in the art, mupirocin is an ideal drug candidate to formulate topical delivery because it has characteristics as log P: 2.45, PKa: 4.83, molecular weight: 500.6 Da, and has less half-life: 20-40 minutes. Therefore, such characteristics favor the mupirocin to formulate as a self-adhesive matrix patch.

Therefore, the present invention discloses a self-adhesive medicated patch that can prevent exit site infections during peritoneal dialysis.

Figure 2:
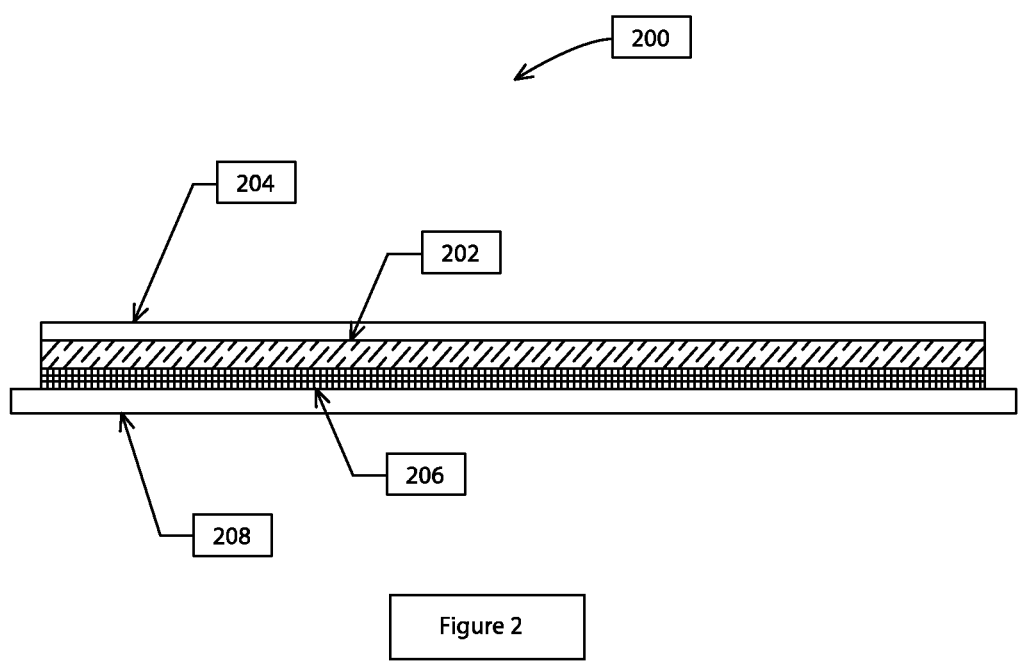
FIG. 2 depicts a schematic of a medicated patch, according to an embodiment of a present invention.

As shown in FIG. 2, the present invention discloses the self-adhesive medicated patch 200 that can prevent exit site infections during peritoneal dialysis. In some embodiments, the patch 200 can be used for topical and other transdermal drug delivery applications/procedures. The patch 200 can cure medical conditions also. The patch 200 is configured to be a medicated patch having a medication which can prevent medical condition such as ESI and peritonitis. In some embodiments, the patch 200 can cure impetigo (school sores); Folliculitis; Furunculosis (boils); Ecthyma; Infected dermatoses such as eczema, psoriasis, atopic dermatitis, epidermolysis bullosa, and ichthyosis; and Infected traumatic lesions such as ulcers, minor burns, abrasions, cuts, wounds.

As shown in FIG. 2, the patch 200 includes a medication layer 202 having the medication contained therein. Examples of the medication may include, but are not limited to mupirocin, or any other prophylactic antibiotics, curcumin or any other antibiotics of natural product origin, and so on. The medication layer 202 provides an adhesive matrix into which the medication is embedded. In an embodiment, the medication that is used in the patch is a natural substance or chemical compound produced by a living organism. In another embodiment, the medication used in the patch is an antibiotic compound that inhibits the growth of or destroys microorganisms. In another embodiment, the medication is mixture of natural origin and of chemical origin.

In some embodiments, the medication layer 202 can be made from materials which include but are not limited to polymers, adhesive polymer, and so on. Examples of the polymers may include but are not limited to Ethyl cellulose, Hydroxy propyl methyl cellulose, Methyl methacrylate, and so on.

In some embodiments, the patch 200 includes a backing layer 204 disposed on one side of the medication layer 202. In some embodiments, the backing layer 204 may be defined as an uppermost layer of the patch 200 which is visible and can be made from materials such as including but are not limited to polyethylene, polypropylene, ethyl vinylacetate copolymer film, and so on.

In some embodiments, the patch 200 provides a protective barrier preventing bacteria to enter therein. For Instance, as the microbes—bacteria or fungi reach inner to the patch 200, the medication starts killing not only *S. aureus* but also against Methicillin-resistant *Staphylococcus aureus* (MRSA). Mupirocin reversibly binds to the isoleucyl t-RNA synthetase in *Staphylococcus aureus*, thereby inhibiting bacterial protein synthesis. Curcumin, a natural product, disrupts the bacterial membrane leading to prevention of biofilm formation. Moreover, the combination of antibiotic with curcumin produces synergistic effect and increases the antibiotic effect.

In some embodiments, the patch 200 has another layer—skin adhesive layer 206 which allows the patch to stick onto the skin, as well as holding the catheter firmly. In some embodiments, the adhesive layer 206 can be made from materials such as including but are not limited to medical-grade adhesives, such as low viscosity dimethylsiloxane, silicone, acrylates, and so on.

The patch 200 further has a protective liner 208 disposed beneath the skin adhesive layer 206. The protective liner 208 is configured to protect the patch 200 from various damages such as contamination from dust and other avoidable contamination. The liner 208 needs to be removed immediately before the application of the patch 200 to the skin. The liner 208 is a primary packaging material and is in intimate contact with the delivery system. Thus, the liner 208 should be chemically inert to the materials used in the patch 200. Cross-linking between adhesion layer 206 and the liner 208 can increase the amount of force needed to remove the liner 208.

In some embodiments, the liner 208 can be made with materials such as including but are not limited to special medical grade, fluorocarbon polyester or siliconized polyester or polyester liner.

In some embodiments, the patch 200 includes chemical enhancers such as menthol or eugenol which can trigger the permeation of the medication into the site of application. For Example, the matrix of the medication layer 202 allows the medication to diffuse into the site of application area i.e. exit site area. The medication is allowed to diffuse from the matrix of the medication layer 202 to the adhesive layer 206, followed by passing into the site of application. The diffusion of the medication release behavior/characteristics is controlled by the optimization of the matrix and adhesive layer 206. Thus controlled release of medication is obtained.

In some embodiments, the patch 200 can be thick as 0.2 mm and diameter can vary in the range of 5-8 cm as per the patient's requirement. In some embodiments, the backing layer 204, the medication layer 202, and the adhesive layer 206 can be as thick as 0.1 mm, and diameter in the range of 5-8 cm, while the liner 208 can be as thick as 0.05 mm and diameter in the range of 5-8 cm.

In some embodiments, a method for manufacturing the patch 200 is disclosed in accordance with the present invention. The method involves dissolving polymer, adhesive and plasticizer in chloroform, forming a solution. Examples of polymers may include but are not limited to Ethyl cellulose polymer, Hydroxy propyl methyl cellulose, Methyl methacrylate, and so on. Examples of adhesives may include but are not limited to medical-grade silicone adhesives, such as low viscosity dimethylsiloxane, silicone, acrylates, and so on. Examples of plasticizers may include but are not limited to triethylcitrate, dibutyl sebacate, propyleneglycol, and so on. The method further includes dissolving the medication into the solution i.e. embedding, forming a final viscous mass. The mass is coated onto the backing layer 204 using film applicator, incorporating the medication layer 202. Thus, the medication is coated such that the medication is distributed uniformly in between the polymer chains of the matrix of the medication layer 202 and is not released from the matrix. The method further includes providing an unmedicated adhesive layer 206 on top of the medication layer 202 for stronger adhesion of the patch 200 onto the catheter and the skin.

In some embodiments, the patch 200 is placed on the catheter by applying pressure to skin of the patient after insertion of the catheter therein, thereby holding the catheter and the medication diffusing into the skin prevents the exit site of infection.

While the preferred embodiment of the present invention and its advantages has been disclosed in the above description, the invention is not limited there to but only by the scope of the appended claim.

As will be readily apparent to those skilled in the art, the present invention may easily be produced in other specific forms without departing from its essential characteristics. The present embodiments are, therefore, to be considered as merely illustrative and not restrictive, the scope of the invention being indicated by the claims rather than the foregoing description, and all changes which come within therefore intended to be embraced therein.

What is claimed is:

1. A medicated apparatus comprising of a medicated surgical patch for use onto a subject undergoing peritoneal dialysis, the medicated surgical patch further comprising:
   a backing film disposed on one side of a medication layer wherein the backing film is made of material that is bio-compatible and the medication layer is made of material that is bio-compatible;
   the medication layer containing a medication therein, wherein the medication layer provides a protective barrier against bacteria, wherein the medication comprising at least one of Mupirocin or Curcumin, wherein the medication layer comprises a matrix to release the medication, wherein the medication layer is formed by coating of a viscous mass on the backing layer, wherein the viscous mass is formed by dissolving the medication in a solution, wherein the solution is formed by dissolving polymer, adhesive and plasticizer in chloroform such that the medication is distributed uniformly in polymer chains of the matrix;
   a skin adhesive layer disposed beneath the medication layer;
   a protective liner disposed beneath the skin adhesive layer, wherein the medication coated and uniformly distributed over the backing layer is allowed to release from the matrix to the skin adhesive layer, followed by passing into a site of application area, wherein the amount of release of the medication into the site of application area is controlled based on size of the matrix and the skin adhesive layer; and
   at least one chemical enhancer, wherein at least one chemical enhancer triggers permeation of the medication into the site of application area, the at least one chemical enhancer comprising eugenol;
   wherein the medicated patch is configured to be placed on a catheter by applying pressure to skin of the subject after insertion of the catheter therein, thereby holding the catheter and the medication diffusing into the skin.

2. The medicated apparatus of claim 1, wherein the medicated surgical patch is self-adhesive, wherein thickness of each of the backing layer, the medication layer, and the skin adhesive layer is 0.1 mm.

3. The medicated apparatus of claim 1, wherein the medication is embedded into an adhesive matrix of the medication layer.

4. The medicated apparatus of claim 1, wherein the medicated surgical patch reduces frequent changing of a catheter at an exit site of peritoneal dialysis.

5. The medicated apparatus of claim 1, wherein the medicated surgical patch reduces frequent changing of a catheter during peritonitis dialysis in the subject.

6. The medicated apparatus of claim 1, wherein the medicated surgical patch reduces infections at an exit site of drainage tubes.

7. The medicated apparatus of claim 1, wherein the medicated surgical patch reduces infections at an exit site of laparoscopic surgical incisions or due to other incisions.

8. The medicated apparatus of claim 3, wherein the medication is coated on the medication layer using a film applicator.

9. The medicated apparatus of claim 3, wherein the medication is a drug, a natural substance, antibiotic, or any medication or combination thereof for prevention of infection.

10. A method for reducing infections by topical drug delivery, the method comprising: providing the medicated patch of claim 1; placing the medicated patch on the catheter by applying the pressure to the medicated patch on the skin of the subject after insertion of the catheter therein; and
    diffusing the medication into the skin for preventing an exit site infection of peritonitis during peritoneal dialysis.

11. The method of claim 10, wherein the medication is loaded using film coating method.

12. The method of claim 10, wherein the infection is peritonitis.

13. The method of claim 10, wherein the peritoneal dialysis is performed.

14. The method of claim 10, wherein the medicated surgical patch reduces infections at exit site in drainage tubes.

15. The method of claim 10, wherein the medicated surgical patch reduces infections at exit site in laparoscopic surgical incisions.

* * * * *